(12) United States Patent
Ricoul et al.

(10) Patent No.: US 9,643,120 B2
(45) Date of Patent: May 9, 2017

(54) GAS CHROMATOGRAPHY COLUMN COMPRISING A POROUS STATIONARY PHASE IN KEEPING THEREWITH

(71) Applicant: Commissariat à l'énergie atomique et aux énergies alternatives, Paris (FR)

(72) Inventors: Florence Ricoul, Quaix-en-chartreuse (FR); Vincent Jousseaume, Le Sappy en Chartreuse (FR); Muriel Matheron, Chambery (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 155 days.

(21) Appl. No.: 14/438,711

(22) PCT Filed: Oct. 30, 2013

(86) PCT No.: PCT/EP2013/072723
§ 371 (c)(1),
(2) Date: Apr. 27, 2015

(87) PCT Pub. No.: WO2014/068004
PCT Pub. Date: May 8, 2014

(65) Prior Publication Data
US 2015/0251127 A1    Sep. 10, 2015

(30) Foreign Application Priority Data
Oct. 31, 2012    (FR) ..................... 12 60403

(51) Int. Cl.
*B01D 53/04*    (2006.01)
*G01N 30/60*    (2006.01)
(Continued)

(52) U.S. Cl.
CPC .......... *B01D 53/0423* (2013.01); *B01J 20/10* (2013.01); *B01J 20/287* (2013.01);
(Continued)

(58) Field of Classification Search
CPC ......... G01N 30/6095; G01N 2030/484; G01N 2030/525; B01J 20/10; B01J 20/28097;
(Continued)

(56) References Cited

U.S. PATENT DOCUMENTS

| 2011/0011157 A1* | 1/2011 | Bourlon | ................ B01J 20/205 73/23.41 |
| 2013/0174642 A1* | 7/2013 | Bourlon | ................ B01J 20/103 73/23.39 |
| 2015/0068280 A1 | 3/2015 | Ricoul | |

FOREIGN PATENT DOCUMENTS

DE    197 26 000 A1    11/1998
WO    2004/065955 A1    8/2004
(Continued)

OTHER PUBLICATIONS

H. Grange et al., "A New Method for Hermeticity Measurements Using Porous Ultra Low k Dielectrics for Sub-PPM Moisture Detection" Transducers, 2009.
(Continued)

*Primary Examiner* — Robert Clemente
(74) *Attorney, Agent, or Firm* — Pearne & Gordon, LLP

(57) ABSTRACT

Gas chromatography column comprising a substrate, a channel formed in said substrate, a cover closing said substrate and a stationary phase covering the walls of said channel, wherein said stationary phase is made of SiOxCyHz with x between 1.6 and 1.8, y between 1 and 2.2 and z between 3 and 4, wherein said stationary phase is porous with a porosity of between 10% and 40%.

10 Claims, 5 Drawing Sheets

(51) Int. Cl.
  *B01J 20/10* (2006.01)
  *B01J 20/28* (2006.01)
  *B01J 20/287* (2006.01)
  *B01J 20/30* (2006.01)
  *B01J 20/32* (2006.01)
  *C23C 16/40* (2006.01)
  *C23C 16/56* (2006.01)

(52) U.S. Cl.
  CPC ..... *B01J 20/28097* (2013.01); *B01J 20/3078* (2013.01); *B01J 20/3085* (2013.01); *B01J 20/3204* (2013.01); *B01J 20/3272* (2013.01); *B01J 20/3291* (2013.01); *C23C 16/401* (2013.01); *C23C 16/56* (2013.01); *G01N 30/6095* (2013.01); *B01D 2253/106* (2013.01); *B01D 2253/311* (2013.01); *B01J 2220/54* (2013.01); *B01J 2220/66* (2013.01)

(58) Field of Classification Search
  CPC .. B01J 20/287; B01J 20/3078; B01J 20/3085; B01J 20/3204; B01J 20/3272; B01J 20/3291; B01D 53/02; B01D 53/0423; B01D 2253/311
  See application file for complete search history.

(56) References Cited

FOREIGN PATENT DOCUMENTS

| WO | 2006/042727 A1 | 4/2006 |
|---|---|---|
| WO | 2011/110345 A1 | 9/2011 |

OTHER PUBLICATIONS

Zhenghua Ji et al., "Porous layer open-tubular capillary columns: preparations, applications and future directions." Journal of Chromatography A., vol. 842, 1999.
V. Jousseaume et al., "Porous ultra low k deposited by PECVD: From deposition to material properties" Surface & Coatings Technology, vol. 201, 2007.
U. Lehmann et al., "A miniaturized gas chromatograph for autonomous and longtime measurements" Sensor 99 Proceedings I, 1999.
S. Nehlsen et al., "Gas permeation properties of plasma polymerized thin film siloxane-type membranes for temperatures up to 350° C." Journal of Membrane Science, vol. 106, 1995.
Yu. V. Patrushev et al., "A Capillary Gas Chromatographic Column with a Porous Layer Based on a Mesoporous Material" Russian Journal of Physical Chemistry A, vol. 82, No. 7, 2008.
Gustavo Serrano et al., "Assessing the reliability of wall-coated microfabricated gas chromatographic separation columns" Sensors and Actuators B: Chemical, vol. 141, 2009.
Jianhai Sun et al., "A high resolution MEMS based gas chromatography column for the analysis of benzene and toluene gaseous mixtures." Sensors and Actuators B: Chemical, vol. 141, 2009.
Jaap De Zeeuw, "The Develeopment and Application of PLOT Columns in Gas-Solid Chromatography" LC-GC Europe, Jan. 2011.
Search Report issued in Application No. FR 12 60403 dated Jun. 26, 2013.
International Search Report issued in Application No. PCT/EP2013/072723 dated Jan. 13, 2014.
Written Opinion issued in Application No. PCT/EP2013/072723 dated Jan. 13, 2014.

* cited by examiner

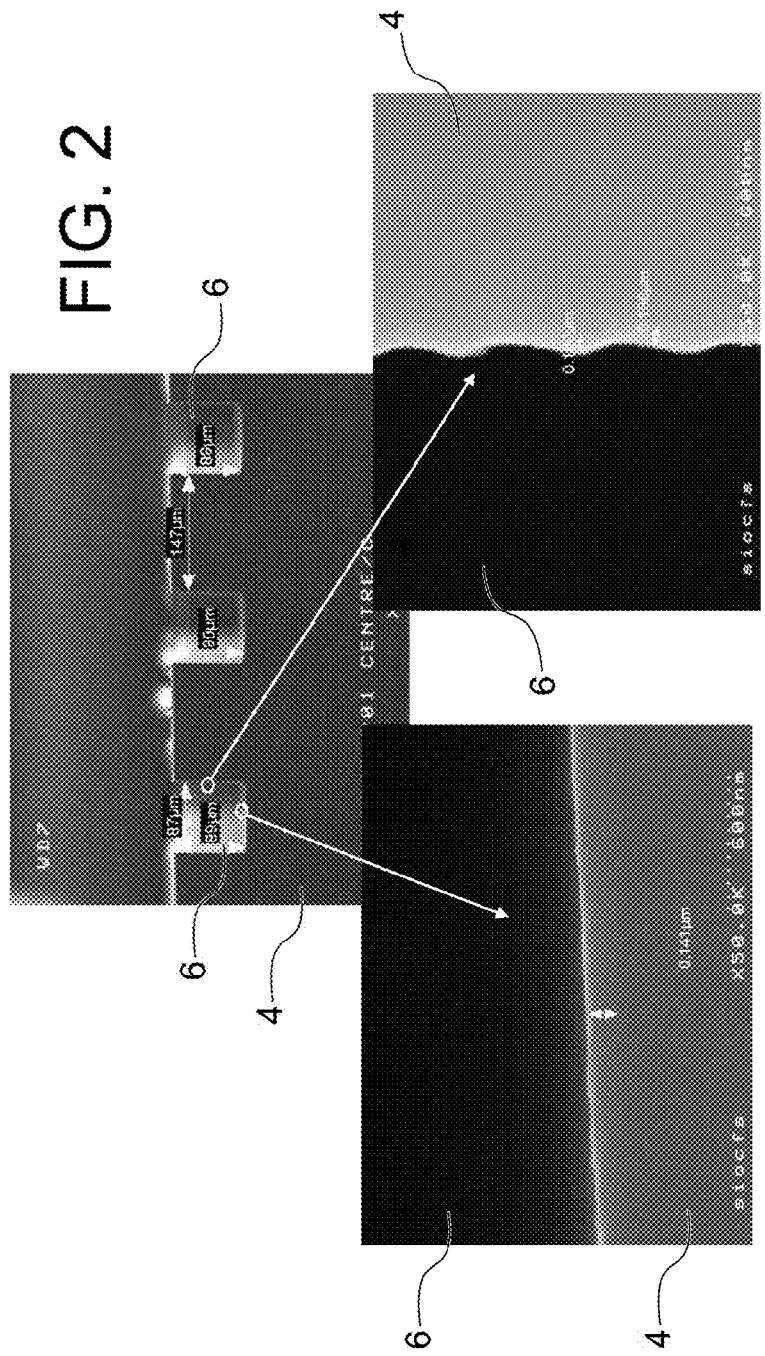

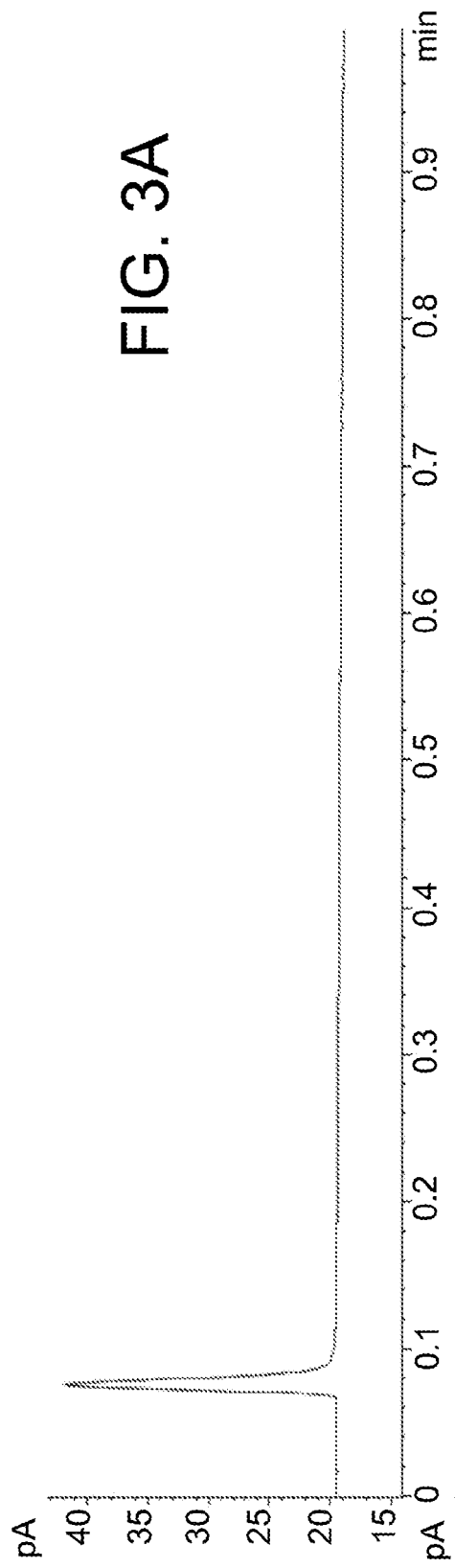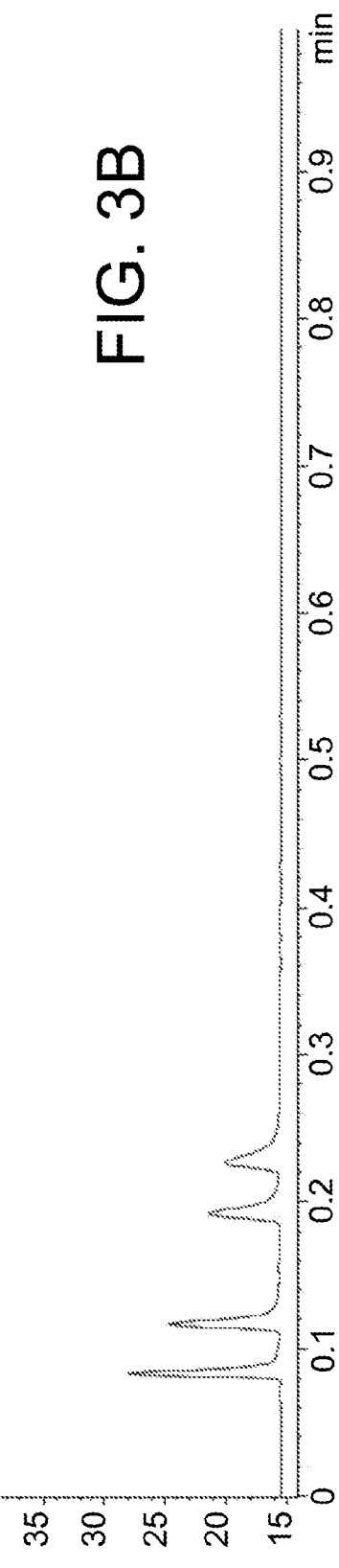

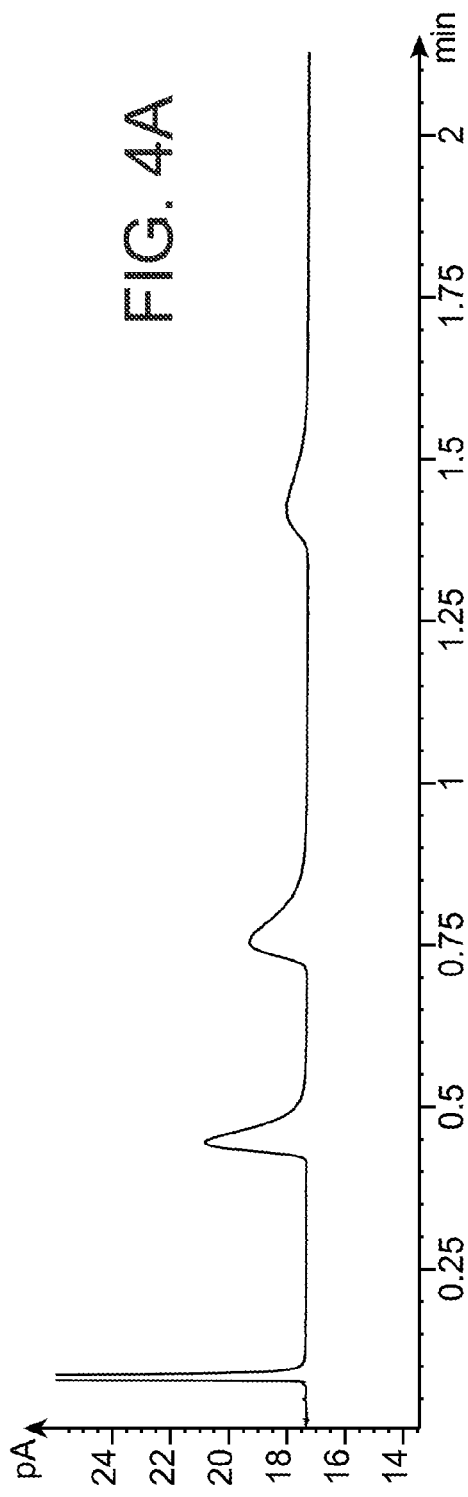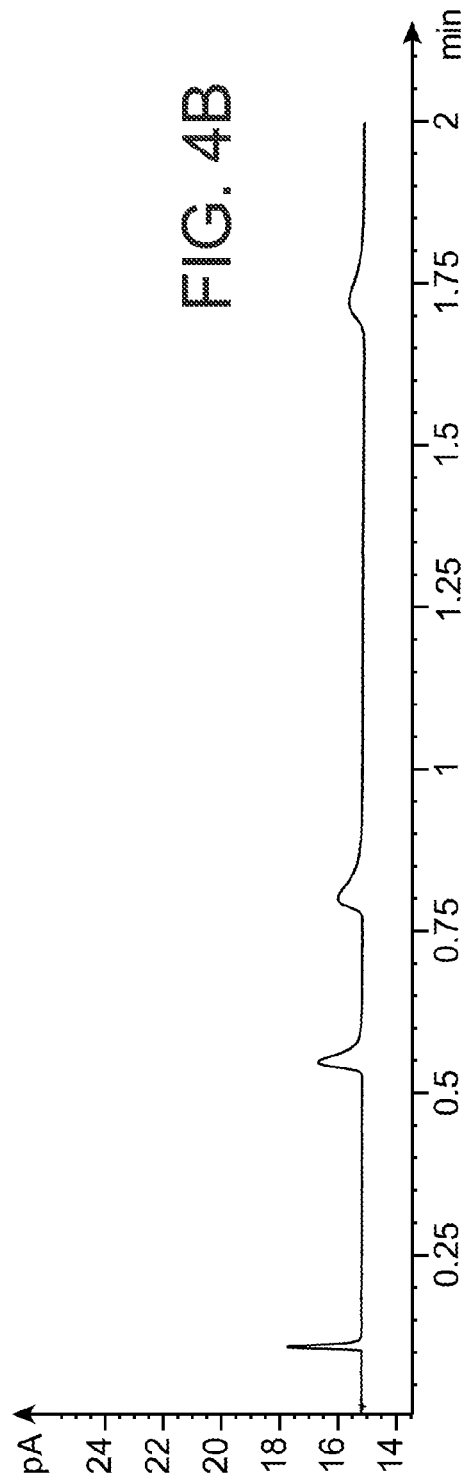

US 9,643,120 B2

GAS CHROMATOGRAPHY COLUMN COMPRISING A POROUS STATIONARY PHASE IN KEEPING THEREWITH

TECHNICAL FIELD AND PRIOR ART

The present invention relates to gas chromatography columns comprising a porous and conformal stationary phase, and in particular to gas chromatography microcolumns.

The technique of gas chromatography is one of the most widely used separation and analysis methods for volatile or semi-volatile compounds. In particular, when it is associated with mass spectrometry, it is the method of choice for the analysis of complex gaseous mixtures in numerous fields, such as the environment, safety, the pharmaceuticals industry, the food processing industry, petrochemicals, etc.

A chromatography column comprises within it a stationary phase having a certain affinity with the compounds to be analysed. It is this affinity which makes it possible to separate the compounds within the column.

However the equipment is for the moment difficult to transport and has a high cost. Research is therefore being carried out to reduce the size of said equipment. Columns of micrometric size for gas phase chromatography have been made in a silicon substrate.

The stationary phase is generally formed after sealing of a cap, by liquid deposition methods, for each column separately with the deposition of a polymer film, for example described in the document Serrano, G., S. M. Reidy, and E. T. Zellers, *Assessing the reliability of wall-coated microfabricated gas chromatographic separation columns. Sensors and Actuators B: Chemical*, 2009. 141(1): p. 217-226. This technique has the drawbacks of forming a stationary layer having poor conformity, i.e. zones of excessive thickness of the film deposited in the corners due to capillary effects, slow rates and low production yields since each column is functionalised separately. Moreover, these methods have poor reproducibility due to vagaries during the drying of the polymer.

To overcome these drawbacks, it has been envisaged to form the stationary phase by gas phase deposition before sealing of a cap. For example, the documents Lehman, U., et al. *A miniaturized gas chromatograph for autonomous and longtime measurements, in Sensor 99*. 1999 and Muller, J. and U. Lehmann, *Trennsäule für eine miniaturisierten Gaschromatographen and verfahren zu deren Herstellung S. M. Technology*, Editor. 1997: Germany describes the functionalization of a column by means of a plasma enhanced chemical vapour deposition (or PECVD). However, the stationary phase is not porous.

DESCRIPTION OF THE INVENTION

It is consequently an aim of the present invention to offer a chromatography column comprising a porous stationary phase, the porosity of which is controlled, in which the deposition is conformal and assures good separation efficiency.

The aforementioned aim is attained by a gas chromatography column comprising a stationary phase made of porous $SiO_xC_yH_z$. The fact of having available a porous stationary phase increases the developed surface thereof, and favours the retention of chemical species, which improves the separation. Furthermore, the inventors reckon that the better controlled the porosity, the better will be the sharpness of the chromatographic peaks. It will then be understood that the efficiency of the column will be improved: at constant column length, the column could separate more chemical species.

The coefficient x is between 1 and 2 and in a preferred manner between 1.6 and 1.8. The coefficient y is between 0.8 and 3 and preferably between 1 and 2.2, and the coefficient z is between 2.5 and 4.5 and preferably between 3 and 4, the limits of the ranges being included.

The inventors have determined that by using $SiO_xC_yH_z$ with the values of x, y, z above, said $SiO_xC_yH_z$ having a porosity of between 10% and 40%, they obtained/formed a particularly efficient stationary phase. Nothing made it possible to envisage that this combination would offer a material as well suited to forming a stationary phase. In fact the behaviour of a material as stationary phase is not predictable, and the inventors have made a triple selection by, at one and the same time, selecting the type of material, i.e. $SiO_xC_yH_z$, by selecting the choice of the values of the coefficients x, y, z and by selecting the choice of the range of values of the porosity of the material ending up in a stationary phase of high efficiency being obtained in an unexpected manner because there was nothing to suggest that the choice of the coefficients and the choice of the value of the porosity applied to this material would make it possible to obtain said efficiency.

This material may advantageously be deposited by chemical vapour deposition, which makes it possible to obtain a conformal deposition. The addition of pore-forming agents during the deposition of $SiO_xC_yH_z$ makes it possible to control the porosity. In an even more advantageous manner, the porous material may be deposited by plasma enhanced chemical vapour deposition, which makes it possible to carry out the deposition at low temperature and thereby to conserve the organic character of the material. This favours the addition of pore-forming agents.

Moreover, the formation of the stationary phase by chemical vapour deposition makes it possible to form several columns collectively. Furthermore, better reproducibility is obtained.

The chromatography column according to the invention makes it possible to separate at least 4000 plates.

Moreover, SiOCH is used in microelectronics in interconnections due to its very low dielectric constant, which offers the advantage of having available a deposition technique that is well controlled industrially. Furthermore, the microcolumns being themselves formed by microelectronic methods, the deposition of $SiO_xC_yH_z$ is integrated in the method of forming microcolumns.

The subject matter of the present invention is therefore a gas chromatography column comprising a substrate, a channel formed in said substrate, a cover closing said substrate and a stationary phase covering the walls of said channel, wherein said stationary phase is made of $SiO_xC_yH_z$ with x between 1 and 2, y between 0.8 and 3 and z between 2.5 and 4.5, the limits of the ranges being included, wherein said stationary phase is porous and has a porosity of between 10% and 40%.

The column is advantageously a chromatography microcolumn.

The stationary phase preferably has a thickness of between 50 nm and 1000 nm.

For example, the substrate is made of silicon and the cap is made of glass or silicon.

Another subject-matter of the present invention is a method of manufacturing a gas chromatography column according to the present invention, comprising the steps of:

a) formation of a channel in a substrate, b) formation of a layer of SiOxCyHz on the walls of said channel, a pore-forming agent being implemented, for example norbornadiene, said layer forming a stationary layer, c) annealing to eliminate the pore-forming agent, d) closing of the channel by putting in place a cap.

Step b) is advantageously carried out by chemical vapour deposition.

In an even more advantageous manner, step b) may be carried out by enhanced chemical vapour deposition.

Step a) is for example carried out by photolithography and etching.

During step b) diethoxymethylsilane may be used as precursor.

Advantageously, several columns are manufactured collectively on a same substrate, the substrate then being divided so as to separate the columns thereby produced.

BRIEF DESCRIPTION OF THE DRAWINGS

The present invention will be better understood by means of the description that follows and the drawings in which:

FIG. 2 is a photo of a transversal section of a chromatography microcolumn comprising a stationary phase made of SiOCH;

FIGS. 2A and 2B are enlarged views of a lateral edge of the bottom respectively of the channel of FIG. 2;

FIG. 3A represents a chromatogram obtained with a microcolumn with a deposition of porous SiOCH of 120 nm for the injection of a BTEX (benzene, toluene, ethyl-benzene, o-xylene) mixture, having a porosity of 30%;

FIG. 3B represents a chromatogram obtained with a microcolumn without stationary phase for the injection of a BTEX (benzene, toluene, ethyl-benzene, o-xylene) mixture;

FIGS. 4A and 4B represent chronograms obtained with a microcolumn with a deposition of porous SiOCH for the injection of a C5-C7-Tol-C8 (pentane, heptane, toluene and octane) mixture, having a porosity of 33% and 20% respectively.

DETAILED DESCRIPTION OF PARTICULAR EMBODIMENTS

Figure 1A:
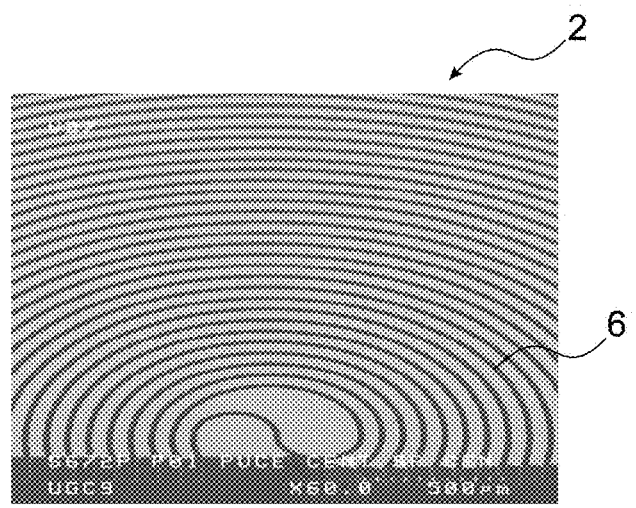
FIG. 1A is a top view of a chromatography microcolumn.
Figure 1B:
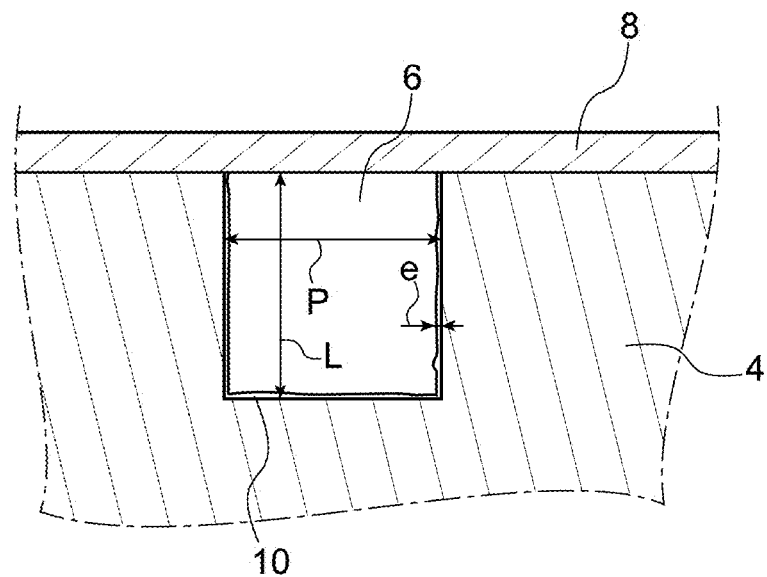
FIG. 1B is a schematic sectional view of a chromatography microcolumn represented partially.

In FIG. 1A may be seen a top view of a gas chromatography microcolumn 2. In FIG. 1B may be seen a transversal section of the microcolumn comprising a substrate 4 in which is formed a channel 6 which generally has a rectangular transversal section, a cap 8 closing the channel in a sealed manner. The cap 8 is attached to the substrate 4 for example by anodic sealing.

The column 2 also comprises fluid connection ends to enable the later connection of the microcolumn to external equipment such as an injection system at the inlet and an analysis system at the outlet, via for example capillaries.

In the example represented, the channel 6 has a spiral profile, it is a spiral having a double winding. Thus, the two connection ends of the channel may be situated on one edge of the substrate. The channel may also have a coil shape or any other geometry making it possible to optimise the length of the channel with respect to the surface of the substrate.

Preferably, the channel 6 has a high form factor, i.e. a ratio depth P over width L preferably greater than 1, even more preferably greater than 10.

The microcolumn also comprises a stationary phase 10 covering the walls of the channel 6.

The stationary phase 10 is a compound of SiOCH type. The term designates a compound of formula SiOxCyHz with:

x between 1 and 2, preferably between 1.6 and 1.8, y between 0.8 and 3, preferably between 1 and 2.2 z between 2.5 and 4.5, preferably between 3 and 4.

The SiOxCyHz is made porous. The stationary phase layer 10 preferably has a thickness e of between 50 nm and 1000 nm, or even between 50 nm and 2000 nm.

The SiOxCyHz has an open porosity, which enables the access into the pores of the chemical species to be separated.

Preferably, the porosity is between 10% and 40%, or even between 10% and 60%. This percentage represents the volume of the pores for a given volume of material. Preferably the pores have a radius between 1 nm and 3 nm, or even between 1 nm and 5 nm. These dimensions have been observed by ellipsoporosimetry, the probe molecule being toluene, the measuring device being the EP12 model—SOPRA firm.

The SiOxCyHz may advantageously be deposited by chemical vapour deposition or CVD. The deposition of SiOxCyHz is then conformal, i.e. it has a homogenous thickness over the entire length of the walls.

Moreover, the addition of a pore-forming agent during the vapour phase deposition makes it possible to control the porosity and to have a low dispersion in the pores of the stationary phase. As indicated previously, the fact of controlling the size, the size dispersion and the spatial distribution of the pores makes it possible to make the chromatographic peaks sharper.

In an even more advantageous manner, it may be deposited by chemical vapour deposition, enhanced for example by plasma, a method known by the acronym PECVD (Plasma-Enhanced Chemical Vapour Deposition), which makes it possible to obtain a more conformal deposition than the sputtering techniques of the prior art. Thus, deposition by CVD or enhanced CVD are well suited to channels having a large form factor. It will be recalled that a deposition by PECVD, or, more generally, by enhanced CVD, makes it possible to carry out the deposition at low temperature and thereby conserve the organic character of the material. This favours the homogeneity of the spatial distribution of the pore-forming agents and, in fine, the homogeneity of the spatial distribution of the pores formed during the elimination of the pore-forming agents.

According to an advantageous variant, the deposition may be carried out by filament assisted chemical vapour deposition or FACVD, which makes it possible to optimise the conformity.

According to another variant, the deposition may be carried out by chemical vapour deposition of a first layer comprising SiOCH and the pore-forming agent, followed by chemical vapour deposition of a second layer so as to constitute a second gas tight layer. A step of foaming is then carried out, which enables the formation of pores in the layer of SiOCH. The second layer is then eliminated.

This method is described in the patent application FR2918997. It enables pores of greater size to be obtained than depositions by CVD or enhanced CVD.

Moreover, the formation of the stationary phase by CVD makes it possible to form several columns collectively. Furthermore, better reproducibility is obtained.

After the step of chemical vapour deposition, the pore-forming agent is eliminated by a thermal method (annealing), potentially enhanced by UV irradiation. During this step, the pore-forming agent disappears, which enables the formation of pores in the matrix.

According to an embodiment, whatever the deposition method implemented, the layer of porous SiOCH may undergo a post-treatment to modify the surface chemical functions. This makes it possible to adjust the selectivity of the stationary phase with respect to a given analyte. An example of post treatment is the application of a $O_2$, He, or $N_2O$ plasma. Another example is a silanisation, that is to say a covalent grafting of organic molecules via a silane function.

In FIG. 2 may be seen a photo of a transversal section of a channel 6, made in a substrate 4, the channel 6 being covered with a stationary phase 5 made of SiOCH. In FIG. 2A may be seen an enlarged view of a lateral edge of the channel of FIG. 2, in which the thickness of the stationary layer is indicated in two spots (0.100 μm and 0.106 μm) and in FIG. 2B may be seen an enlarged view of the bottom on which the thickness of the stationary layer is 0.140 μm. The stationary phase is delimited schematically by a broken line. A low variation of this thickness is thus observed. The calculation of the conformity is 0.7: this is the ratio of the lowest thickness of the layer over the highest thickness, these thicknesses being measured over the section of the channel. By comparison, when a deposition is carried out by liquid deposition method, the conformity observed is less than 0.05. On the bottom.

The formation of the stationary phase by chemical vapour deposition enables a formation of several columns simultaneously, for example in the case of microcolumns formed in a substrate made of silicon. The stationary phases of all the microcolumns formed on a wafer made of silicon may be formed simultaneously.

Moreover, chemical vapour deposition offers good reproducibility from one wafer to the next.

Thanks to the invention, columns may be formed offering good separation efficiency, for example more than 4000 plates per meter.

In FIG. 3B may be seen a chromatogram obtained with a microcolumn comprising a stationary phase made of porous SiOCH of 120 nm thickness, following the injection of a BTEX (benzene, toluene, ethyl-benzene, o-xylene) mixture, the SiOCH having a porosity of 30%.

The injection conditions are the following: the temperature of the column is 60° C., the carrier gas is helium at 20 psi (that is to say a column flow rate of around 0.5 ml/min), 0.01 μl of BTEX mixture (i.e. around ~3.5 ng of each compound injected into the column).

For the formation of chromatograms, the detector connected at the output of the column is a FID type detector; the column has a length of 1.3 m, a depth of 80 μm and a width of 80 μm.

In FIG. 3A, the chromatogram is obtained with a microcolumn without stationary phase.

It may be noted that the column with the stationary phase made of SiOCH with a porosity of 30% makes it possible to separate very efficiently the compounds of the BTEX mixture whereas the column without stationary phase does not carry out any separation.

Figure 3C:
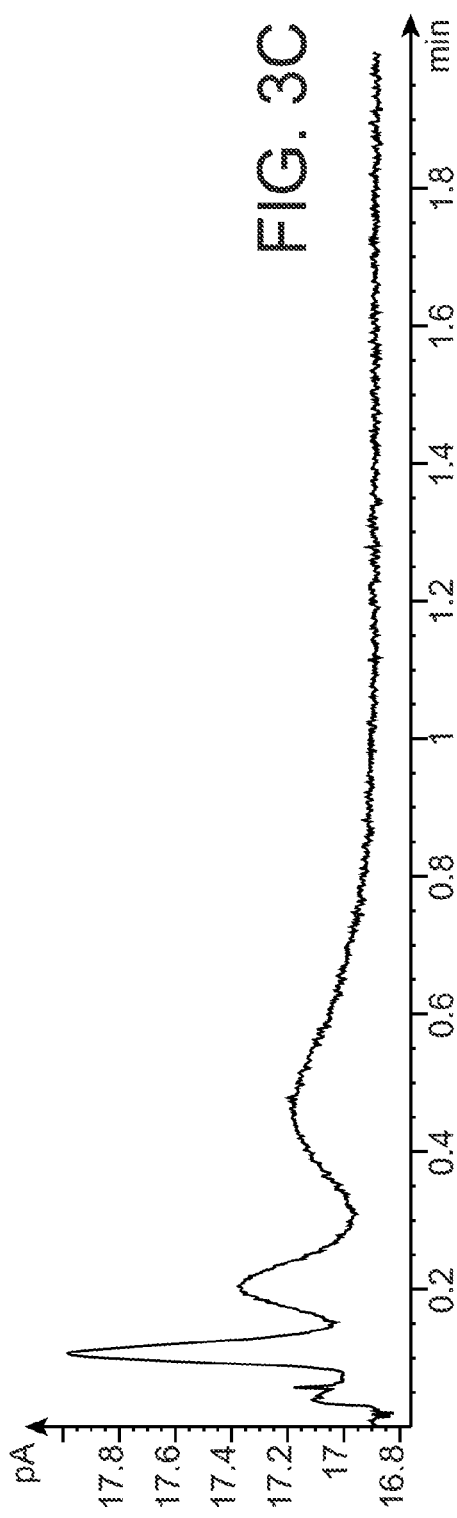
FIGS. 3C and 3D represent chronograms obtained with a microcolumn with a deposition of porous SiOCH of 120 nm for the injection of a BTEX (benzene, toluene, ethyl-benzene, o-xylene) mixture, having a porosity of 3% and 1% respectively.
Figure 3D:
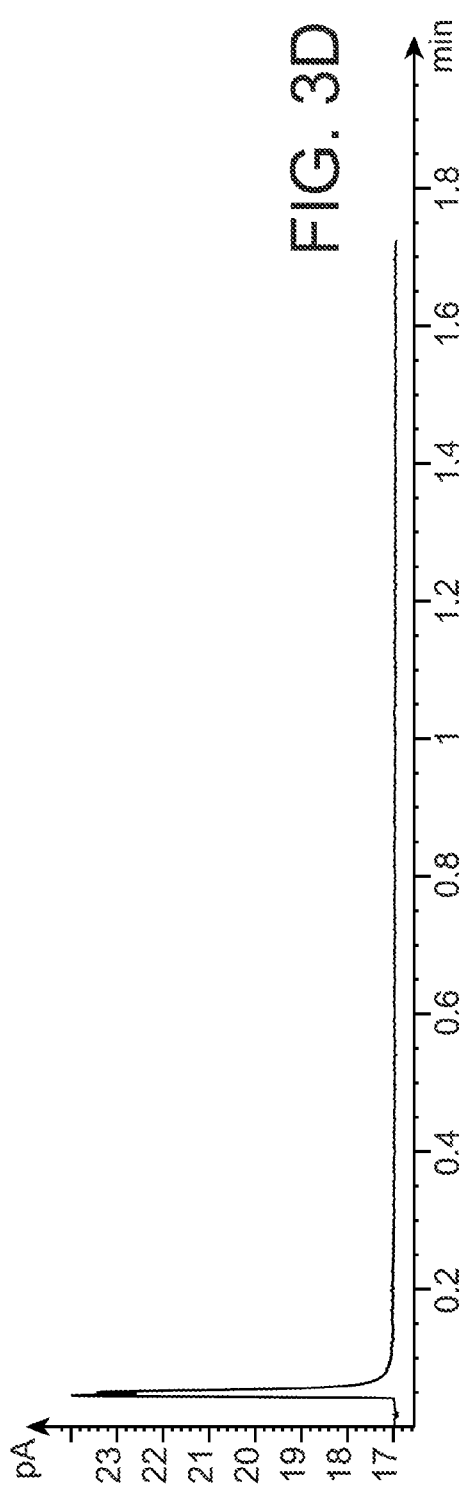

FIGS. 3C and 3D represent chromatograms obtained on the same microcolumns as previously, with respectively a deposition of porous SiOCH with 3% porosity and a deposition of porous SiOCH with 1% porosity for the injection of a BTEX (benzene, toluene, ethyl-benzene, o-xylene) mixture.

It may be noted that a layer of SiOCH having a porosity of 3% does not assure satisfactory separation of the compounds. A column comprising a layer of SiOCH having a porosity of 1% is equivalent to a column without stationary layer.

In FIGS. 4A and 4B may be seen chronograms obtained with microcolumns according to the invention. The inner surface of the column used for the chronogram of FIG. 4A is covered with a stationary phase of SiOCH the porosity of which is 33%. The inner surface of the column used for the chronogram of FIG. 4B is covered with a stationary phase of SiOCH, the porosity of which is 20%.

A C5-C7-Tol-C8 (pentane, heptane, toluene and octane) mixture is injected, with a flow rate of 0.5 ml/m, into the columns in which the temperature of the column is 40° C.

FIGS. 4A and 4B also illustrate the efficiency of the columns with porous SiOCH according to the invention in the separation of the analytes, in the present case, those of the C5-C7-Tol-C8 mixture.

Consequently, the choice of SiOxCyHz, the values of the coefficients x, y and z and the value of the porosity make it possible to form a stationary layer with great efficiency and does so in an unexpected manner.

An example of method of formation of the microcolumn according to the invention will now be described.

In this embodiment example, the microcolumns are formed in a silicon wafer. Several columns are formed on a same wafer, for example 35 columns may be formed on a same wafer.

The formation of one column will be described, but it will be understood that several columns may be formed simultaneously.

During a first step, the channel is etched in the wafer made of silicon.

For example, a photolithography is carried out then an etching, for example a deep reactive ion etching or DRIE.

During a following step, the stationary phase made of SiOCH is deposited, for example by PECVD, for example with a Producer SE installation of the firm Applied Materials.

DEMS (diethoxymethylsilane) is used for example as precursor for the matrix. Potentially it also possible to use other organosilane precursors such as tetramethyl-cyclo-tetrasiloxane, dimethyl-dioxiranyl-silane, diethoxy-methyl-oxiranyl-silane, etc.).

The pore-forming agent is for example norbornadiene (NBD). Other pore-forming agents may be used, for example organic molecules such as norbornene, alpha terpinene, cyclohexene oxide, cyclopentene oxide, trivertal.

As an example, the conditions used for the deposition by PECVD are:

temperature of the substrate: 300° C.
pressure in the chamber 7 Torr,
power of the plasma 630 W,
flow of $O_2$ 175 sccm,
flow of DEMS (100 to 2000 sccm),
flow of NBD (0 to 2000 scm).

The deposition step is followed by an annealing step, which enables the elimination of the pore-forming agent and the formation of the pores, since it does not withstand high temperature, and to cross-link the matrix. The substrate is for example subjected for several minutes to UV at a temperature of the order of 400° C.

During a following step, a cap 8 for example made of glass or made of silicon is sealed onto the substrate so as to close the channel 6. This may be sealed for example by anodic sealing, adhesive serigraphy, lamination of a polymer film, molecular sealing. A step of pre-treatment of the sealing surfaces may potentially take place before the sealing. This may be a plasma treatment (helium, oxygen, etc.) or chemical treatment designated by the term Piranha (application of a liquid $H_2O_2+H_2SO_4$ mixture). This enables a surface cleaning and consequently improves the contact between the substrate and the cap during sealing.

In the case where several columns are formed simultaneously on a same wafer, the columns thereby formed equipped with their cap 8 are cut up so as to obtain individual microcolumns.

As an example, the dimensions of the channels are: a depth h of between 50 μm and 200 μm, a length of between 0.5 m and 3 m, and a width L of between 20 μm and 120 μm.

It will be understood that the invention is not limited to gas chromatography microcolumns but to any gas chromatography column. Nevertheless, it has an additional advantage for microcolumns.

In the case of a capillary column, the SiOCH layer may in particular be applied by sol-gel, the pore-forming agent being initially mixed in the sol, then eliminated after the gelling.

The chromatography column according to the invention is intended to form part of an analysis system, serving to separate the compounds of a mixture. The mixture is transported inside the column by a carrier gas, for example helium.

The column is thus intended to be arranged between an injector connected at the inlet of the column to inject the mixture to be analysed, a system for regulating the carrier gas which injects the carrier gas into the column and a detector that is connected at the outlet of the column and analyses the compounds separated by the column. A system for regulating the temperature of the column may be provided.

The analysis system thereby formed may be used for gas analysis in different application areas such as the environment, safety, health, the pharmaceuticals industry, the food processing industry, petrochemicals, etc.

What is claimed is:

1. Gas chromatography column comprising:
   a substrate, a channel formed in said substrate,
   a cap closing said substrate,
   a stationary phase covering the walls of said channel, said stationary phase being made of SiOxCyHz with x between 1 and 2, y between 0.8 and 3 and z between 2.5 and 4.5, the limits of the ranges being included, said stationary phase having a porosity of between 10% and 40%.

2. Gas chromatography column according to claim 1, being a chromatography microcolumn.

3. Gas chromatography column according to claim 1, in which the stationary phase has a thickness of between 50 nm and 1000 nm.

4. Gas chromatography column according to claim 1, in which the substrate is made of silicon and the cap is made of glass or silicon.

5. Method of manufacturing a gas chromatography column according to claim 1, comprising the steps of:
   a) forming a channel in a substrate,
   b) forming a layer of SiOxCyHz on the walls of said channel, a pore-forming agent being implemented during the formation of the layer of SiOxCyHz, for example norbornadiene,
   c) annealing to eliminate the pore-forming agent,
   d) closing of the channel by putting in place a cap.

6. Method of manufacture according to claim 5, in which step b) is carried out by chemical vapour deposition.

7. Method of manufacture according to claim 5, in which step b) is carried out by enhanced chemical vapour deposition.

8. Method of manufacture according to claim 5, in which step a) is carried out by photolithography and etching.

9. Method of manufacture according to claim 5, in which during step b) diethoxymethylsilane is used as precursor.

10. Method of manufacture according to claim 5, in which several columns are manufactured collectively on a same substrate, the substrate then being divided so as to separate the columns thereby produced.

* * * * *